(12) United States Patent
Schwindeman et al.

(10) Patent No.: US 6,770,587 B1
(45) Date of Patent: Aug. 3, 2004

(54) CHAIN EXTENDED FUNCTIONALIZED INITIATORS AND METHODS OF PREPARING AND USING THE SAME

(75) Inventors: James A. Schwindeman, Lincolnton, NC (US); Randy W. Hall, Kings Mountain, NC (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 09/625,787

(22) Filed: Jul. 26, 2000

(51) Int. Cl.$^7$ ................................................. B01J 31/12
(52) U.S. Cl. ........................................ 502/157; 568/687
(58) Field of Search ........................... 502/157; 568/687

(56) References Cited

U.S. PATENT DOCUMENTS 5,798,418 A   8/1998   Quirk

FOREIGN PATENT DOCUMENTS

| WO | WO 97/05173 A | 2/1997 |
| WO | WO 97/05174 A | 2/1997 |
| WO | WO 97/05179 A | 2/1997 |
| WO | WO 97/06188 A | 2/1997 |
| WO | WO 97/06192 A | 2/1997 |
| WO | WO 97/16465 A | 5/1997 |
| WO | WO 00/50478 A | 8/2000 |

OTHER PUBLICATIONS

Gardette et al., "Vinyl copper reagents 17 Carbocupration of alkynes by organocuprates and—connet derivatives," *Tetrahedron Lett.*, (1982), 23(49), 5155–8, vol. 23, No. 49, 1982, pp. 5156–5158.

Gardette et al., "Alkenylcopper reagents. 26. Carbocupration of alkynes by organocopper reagents bearing a protected hydroxy or thiol function," *Tetrahedron*, vol. 41, No. 24, 1985, pp. 5887–5899.

Tellier et al., "Synthesis of fluorocodlemones," *J. Organomet. Chem.*, vol. 364, No. 1–2, 1989, pp. 17–28.

Schulz et al., "Anionic polymerization initiators containing protected functional groups and functionally terminated diene of polymers," *J. Polym. Sci., Polym. Chem. Ed.*, vol. 12, No. 1, 1974, pp. 153–166.

*Primary Examiner*—Jeffrey Mullis
(74) *Attorney, Agent, or Firm*—Myers Bigel Sibley & Sajovec, PA

(57) ABSTRACT

The present invention provides protected functionalized polymerization initiators having less than one molar equivalent chain extension agent introduced therein to provide hydrocarbon solubility.

4 Claims, No Drawings

CHAIN EXTENDED FUNCTIONALIZED INITIATORS AND METHODS OF PREPARING AND USING THE SAME

FIELD OF THE INVENTION

The present invention relates to functionalized initiators useful in anionic polymerizations and processes for making and using the same.

BACKGROUND OF THE INVENTION

A variety of initiators, which contain oxygen, sulfur, or nitrogen functionality, have been developed for anionic polymerization. This allows the quantitative introduction of a functional group into the head of the living polymer chain so that each growing chain contains a functional group from the initiator. See U.S. Pat. Nos. 5,496,940 and 5,600,021. Exemplary protected functionalized initiators include compounds of the following formula:

and

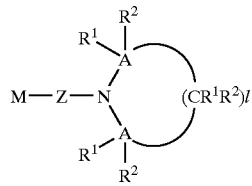

wherein: M is an alkali metal selected from lithium, sodium and potassium; Z is a branched or straight chain hydrocarbon connecting group which contains 3–25 carbon atoms; T is selected from oxygen, sulfur, or nitrogen groups and mixtures thereof; $(A-R^1R^2R^3)_m$ is a protecting group in which A is an element selected from Group IVa of the Periodic Table of the Elements, and $R^1$, $R^2$, and $R^3$ are independently defined as hydrogen, alkyl, substituted alkyl groups containing lower alkyl, lower alkylthio, and lower dialkylamino groups, aryl or substituted aryl groups containing lower alkyl, lower alkylthio, lower dialkylamino groups, or cycloalkyl and substituted cycloalkyl groups containing 5 to 12 carbon atoms; l is an integer from 1 to 7; and m is 1 when T is oxygen or sulfur, and 2 when T is nitrogen.

These functionalized initiators offer numerous advantages over previous anionic polymerization initiators. Such initiators, however, have limited solubility in hydrocarbon solvents. For instance, one such initiator 3-(hexamethyleneimino)-1-propyllithium has a maximum solubility in cyclohexane of 0.30 Molar. Similarly, the maximum solubility of 3-(1,1-dimethylpropyloxy)-1-propyllithium in cyclohexane is 0.30 Molar.

The addition of at least one equivalent of a conjugated diene or an alkenyl substituted aromatic compound can increase the solubility of these initiators in hydrocarbon solutions three to ten fold. The resultant initiators are generally referred to as "chain extended" functionalized initiators. See U.S. Pat. Nos. 5,527,753, 5,565,526, 5,708, 092 and 5,821,307. In each case, at least one equivalent of the chain extension agent is added to the initiator, as represented by "Q" and "n" in the following formula:

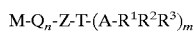

or

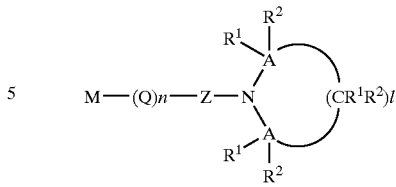

wherein:
M, Z, T, A, $R^1$, $R^2$, $R^3$, l and m are the same as defined above;
Q is an unsaturated hydrocarbyl group derived by incorporation of one or more conjugated diene hydrocarbons, one or more alkenylaromatic compounds, or mixtures of one or more dienes with one or more alkenylaromatic compounds into the M-Z linkage; and
n is an integer from 1 to 5.

Thus, prior chain extended initiators included at least one, and up to five, equivalents of the chain extension agent. The addition of one or more equivalents of the chain extension agent was beneficial for the enhancement of initiator's solubility in hydrocarbon medium. However, despite the advantages of the "chain extension" technology, some drawbacks became apparent for the commercialization of this technology.

For example, the addition of at least one equivalent of the chain extension agent increased the cost of the raw materials required for the initiator formulation. The addition of larger quantities of the chain extension agent also increased the cycle time required for the initiator synthesis in the plant. This led to increased costs of the initiators. In addition, the overall exothermicity of the process was also increased by the addition of larger quantities of the chain extension agent. This caused increased safety concerns as these processes were scaled up. Further, when greater than one equivalent of the chain extension agent was added, low filtration rates were sometimes encountered. This was due to the formation of higher oligomers during the chain extension process.

SUMMARY OF THE INVENTION

Unexpectedly, it has been found that adding less than one equivalent of a chain extension agent to a protected functionalized initiator can be sufficient to significantly increase the solubility of the initiator in hydrocarbon solutions. This is contrary to the expectation that at least one equivalent chain extension agent would be necessary to improve initiator solubility. The use of less than one equivalent chain extension agent provides several benefits, including improved economies of manufacture. In addition, use of less than one equivalent chain extension agent can minimize or eliminate oligomer formation, and the manufacturing problems, particularly on a commercial scale, associated with the same.

The present invention also provide methods for making the novel initiators as well as methods of using the same and polymers produced using the initiators. The chain extended initiators can be prepared, for example, by reacting an omega-protected functionalized haloalkyl with an alkali metal, such as lithium metal, in an inert solvent to form a composition which includes the non-chain extended initiator. The non-chain extended initiator can be recovered from reaction byproducts and excess alkali metal, and the chain extension agent added to the composition. Alternatively the chain extension agent can be added to the non-chain extended initiator composition prior to filtration

DETAILED DESCRIPTION OF THE INVENTION

The present invention now will be described more fully hereinafter, in which preferred embodiments of the invention are shown, This invention may, however, be embodied in many different forms and should not be construed as limited to the embodiments set forth herein; rater, these embodiments are provided so that this disclosure will be thorough and complete, and will fully convey the scope of the invention to those skilled in the art.

The functionalized initiators of the invention thus include a chain extension formed by incorporation of less than 1 molar equivalent of a chain extension agent. The initiators of the invention can be represented by the following formula:

(I)

or

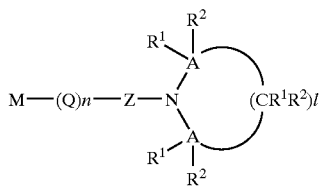

(II)

wherein:
- M is an alkali metal selected from the group consisting of lithium, sodium and potassium;
- Q is a saturated or unsaturated hydrocarbyl group derived by incorporation of one or more conjugated diene hydrocarbons, one or more alkenylsubstituted aromatic compounds, or mixtures of one or more dienes with one or more alkenylsubstituted aromatic compounds into the M-Z linkage;
- Z is a branched or straight chain hydrocarbon connecting group which contains 3–25 carbon atoms, optionally containing aryl or substituted aryl groups;
- T is selected from the group consisting of oxygen, sulfur, and nitrogen groups and mixtures thereof;
- $(A-R^1R^2R^3)_m$ is a protecting group in which A is an element selected from Group IVa of the Periodic Table of the Elements, and $R^1$, $R^2$, and $R^3$ are independently defined as hydrogen, alkyl, substituted alkyl, aryl, substituted aryl, cycloalkyl and substituted cycloalkyl;
- is an integer from 1 to 7;
- n is >0 and <1; and
- m is 1 when T is oxygen or sulfur, and 2 when T is nitrogen.

As used herein, the term "alkyl" refers to straight chain and branched C1–C25 alkyl. The term "substituted alkyl" refers to C1–C25 alkyl substituted with one or more lower C1–C10 alkyl, lower alkylthio, or lower dialkylamino. The term "cycloalkyl" refers to C5–C12 cycloalkyl. The term "substituted cycloalkyl" refers to C5–C12 cycloalkyl substituted with one or more lower C1–C10 alkyl, lower alkylthio, or lower dialkylamino. The term "aryl" refers to C5–C25 aryl having one or more aromatic rings, each of 5 or 6 carbon atoms. Multiple aryl rings may be fused, as in naphthyl or unfused, as in biphenyl. The term "substituted aryl" refers to C5–C25 aryl substituted with one or more lower C1–C10 alkyl, lower alkylthio, or lower dialkylamino. Exemplary aryl and substituted aryl groups include, for example, phenyl, benzyl, and the like.

As noted above, the addition of less than one equivalent of chain extension agent into the structure of the functionalized initiators has been found to be sufficient to significantly increase the solubility of the initiator in hydrocarbon solution. For example, the solubility of 3-(1,1-dimethylethoxy)-1-propyllithium was investigated in cyclohexane at 0° C., with various amounts of isoprene added as a chain extension agent. The solubility data is collected in the table below:

| Isoprene Equivalents | Moles Active/Kg. | Moles Active/Liter |
|---|---|---|
| 0.00 | 0.36 | 0.30 |
| 0.50 | 1.35 | 1.06 |
| 0.75 | 1.72 | 1.33 |
| 1.00 | 1.84 | 1.42 |
| 2.00 | 1.90 | 1.46 |

This data clearly indicates the increased solubility of the initiator in the cyclohexane with the addition of limited amounts of the chain extension agent. A similar impact on the solubility of 3-(hexamethyleneimino)-1-propyllithium in cyclohexane was obtained with the addition of limited amounts of isoprene. This data is collected in the table below:

| Isoprene Equivalents | Moles Active/Kg. | Moles Active/Liter |
|---|---|---|
| 0.00 | 0.20 | 0.16 |
| 0.13 | 0.64 | 0.51 |
| 0.51 | 2.08 | 1.62 |
| 0.90 | 2.43 | 2.01 |
| 2.00 | 2.75 | 2.28 |

This data clearly indicates the increased solubility of the initiator in the cyclohexane with the addition of limited amounts of the chain extension agent. In addition, it was found that the addition of less than one equivalent of the chain extension agent increased the solubility of 2,2-dimethyl-3-trimethylsilyloxy-1-propyllithium.

The organoalkali metal initiators of the formulae

(I)

or

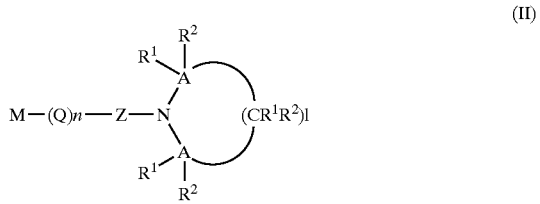

(II)

are prepared by reacting a compound of the formulae

(III)

or

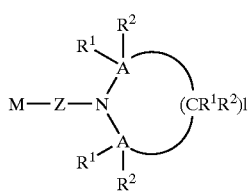

(IV)

wherein M, Z, T, A, $R^1$, $R^2$, $R^3$, l, and m have the meanings ascribed above, with one or more conjugated diene hydrocarbons, one or more alkenylsubstituted aromatic compounds, or mixtures of one or more dienes with one or more alkenylsubstituted aromatic compounds, to form an extended hydrocarbon chain between M and Z in formulae (III) and (IV), which extended chain is denoted as $Q_n$ in formula (I) and (II).

The compounds of formulae (III) and (IV) are prepared by reacting in an inert solvent a selected omega-tertiary-amino-1-haloalkane, an omega-hydroxy-protected-1-haloalkane or an omega-thio-protected-1-haloalkane, depending on whether "T" is to be N, O or S, (the alkyl portions of the haloalkyl groups contain 3 to 25 carbon atoms) with an alkali metal, preferably lithium, at a temperature between about 25° C. and about 130° C., preferably at the solvent reflux temperature, to form a protected monofunctional organoalkali metal initiator (of formulae III or IV), which is not chain extended. The alkali metal can have a particle size between about 10 and 300 microns.

The non-chain extended initiator is reacted with a one or more conjugated diene hydrocarbons, one or more alkenyl-substituted aromatic compounds, or mixtures of one or more dienes with one or more alkenylsubstituted aromatic compounds, advantageously in a predominantly alkane, cycloalkane, or aromatic reaction solvent of 5 to 10 carbon atoms, and mixtures of such solvents, to produce a monofunctional initiator with an extended chain or tether between the metal atom (M) and element (T) in formula (I) and (II) above and mixtures thereof with compounds of Formulae (III) and (IV). The chain extension reaction can be performed in several different manifolds.

In one embodiment, a dilute solution of the non-chain extended initiator can be separated from solid excess alkali metal and co-product alkali metal halide (for example, the excess lithium metal and lithium chloride by-product when a lithium metal dispersion is used). The chain extension agent can then be added to the solution to increase the solubility of the non-chain extended initiator. Optionally, the concentration can be adjusted by removal of at least a portion of the solvent. In another embodiment, the chain extension agent is added to the reaction mixture prior to filtration to remove the excess alkali metal and co-product alkali metal halide.

The chain extension can be carried out under a variety of conditions. Generally the chain extension reaction can be conducted at temperatures ranging from about −30° C. to about 150° C. The chain extension may also be conducted in the presence of certain Lewis bases, generally at temperatures sufficient to slow down polymerization, relative to chain extension. In this aspect of the invention, the Lewis base may be one or more ethers, advantageously one or more aliphatic ethers, such as but not limited to diethyl ether, dimethyl ether, methyl tertiary butyl ether (MTBE), tetrahydrofuran (THF), 2-methyltetrahydrofuran, and the like and mixtures thereof. The Lewis base may also be one or more tertiary amines, such as aliphatic amines selected from the group consisting of trimethylamine, triethylamine, dimethylbutylamine, N,N,N',N'-tetramethylethylenediamine (TMEDA), and the like as well as mixtures thereof. The proportion of these Lewis bases to the organometallic being chain extended may be varied from about 0.05 mole to about 5.0 moles per mole of organometallic. The reaction temperature used in the presence of the Lewis base may be lowered to about −30° C. to about +30° C. to prevent attack by the organometallic on the Lewis base. As the skilled artisan will appreciate, however, the process conditions can depend on various factors such as the nature of Lewis base, the nature of the organometallic, and the ratio of the Lewis base to the organometallic, and can vary from the ranges given above.

In addition, as noted above, the chain extension reaction can be carried out either prior to isolation of the organometallic species from the solid excess alkali metal and co-product alkali metal halide, or subsequent to the filtration. It is noted that not all of the initiator of formulae (III) or (IV) must be chain extended, and the mixtures of chain extended and non-chain extended initiators can also provide benefits.

Incorporation of Q groups into the M-Z linkage to form the compounds of formulae (I) or (II) above involves addition of compounds of the formulae

or

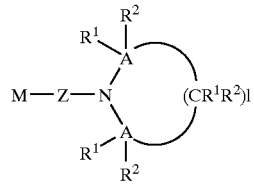

(IV)

wherein the symbols have the meanings ascribed above, across the carbon to carbon double bonds in compounds selected from the consisting of one or more conjugated diene hydrocarbons, one or more alkenylsubstituted aromatic compounds, or mixtures of one or more dienes with one or more alkenylsubstituted aromatic compounds to produce new carbon-metal bonds of an allylic or benzylic nature, similar to those found in a propagating polyalkadiene or polyarylethylene polymer chain derived by anionic initiation of the polymerization of conjugated dienes or arylethylenes. These new carbon-metal bonds are now "activated" toward polymerization and so are much more efficient in promoting polymerization than the precursor M-Z bonds, themselves.

The conjugated diene hydrocarbons used in producing the initiators of this invention are chosen from the group of unsaturated organic compounds that can be polymerized anionically in a reaction initiated by an alkali metal or its carbanionic derivative. Exemplary conjugated diene hydrocarbons include, but are not limited to, 1,3-butadiene, isoprene, 2,3-dimethyl-1,3-butadiene, 1,3-pentadiene (piperylene), myrcene, 2-methyl-3-ethyl-1,3-butadiene, 2-methyl-3-ethyl-1,3-pentadiene, 1,3-hexadiene, 2-methyl-1,3-hexadiene, 1,3-heptadiene, 3-methyl-1,3-heptadiene, 1,3-octadiene, 3-butyl-1,3-octadiene, 3,4-dimethyl-1,3-hexadiene, 3-n-propyl-1,3-pentadiene, 4,5-diethyl-1,3-octadiene, 2,4-diethyl-1,3-butadiene, 2,3-di-n-propyl-1,3-butadiene, 2-methyl-3-isopropyl-1,3-butadiene, and the like and mixtures thereof. Other conjugated diene hydrocarbons can also be useful in practicing this invention, such as those disclosed in U.S. Pat. No. 3,377,404.

The polymerizable alkenylsubstituted aromatic hydrocarbons useful in producing the chain extended initiators of this invention include, but are not limited to, styrene, alpha-methylstyrene, vinyltoluene, 2-vinylpyridine, 4-vinylpyridine, 1-vinylnaphthalene, 2-vinylnaphthalene, 1-alpha-methylvinylnaphthalene, 2-alpha-methylvinylnaphathalene, 1,2-diphenyl-4-methyl-1-hexene, and the like and mixtures of these, as well as alkyl, cycloalkyl, aryl, alkaryl and aralkyl derivatives thereof in which the total number of carbon atoms in the combined hydrocarbon constituents is generally not greater than 18. Examples of these latter compounds include without limitation 3-methylstyrene, 3,5-diethylstyrene, 2-ethyl4-benzylstyrene, 4-phenylstyrene, 4-p-tolylstyrene, 2,4-divinyltoluene, 4,5-dimethyl-1-vinylnaphthalene, and the like and mixtures thereof. Reference is made to U.S. Pat. No. 3,377,404 for disclosure of additional alkenyl substituted aromatic compounds. Non-polymerizable conjugated dienes and alkenyl substituted aromatic compounds including but not limited to 1,1-diphenylethylene and 2,4-hexadiene may also be employed as chain extension agents in accordance with the present invention.

The inert solvent employed during the preparation of the initiators of the present invention, or in subsequent polymerizations as discussed in more detail below, is preferably a non-polar solvent such as a hydrocarbon, since anionic polymerization in the presence of such non-polar solvents is known to produce polyenes with high 1,4-contents from 1,3-dienes. Inert hydrocarbon solvents useful in practicing this invention include but are not limited to inert liquid alkanes, cycloalkanes, aromatic solvents and mixtures thereof. Exemplary alkanes and cycloalkanes can contain five to ten carbon atoms, such as but not limited to pentane, hexane, cyclohexane, methylcyclohexane, heptane, methylcycloheptane, octane, decane and the like as well as mixtures thereof. Exemplary aromatic solvents can contain six to ten carbon atoms, such as but not limited to benzene, toluene, ethylbenzene, p-xylene, m-xylene, o-xylene, n-propylbenzene, isopropylbenzene, n-butylbenzene, and the like, and mixtures thereof.

In addition to novel chain extended functionalized initiators and methods of making the same, the present invention also provides methods for the anionic polymerization of anionically polymerizable monomers and the resultant polymers. This aspect of the invention includes initiating polymerization of a conjugated diene hydrocarbon monomer, a mixture of conjugated diene monomers, an alkenyl substituted aromatic compound, a mixture of alkenyl substituted aromatic compounds, or a mixture of one or more conjugated diene hydrocarbons and one or more alkenyl substituted aromatic compounds in a hydrocarbon or mixed hydrocarbon-polar solvent medium at a temperature of about 10° C. to about 150° C. with one or more initiators as described herein having the formula:

$$\text{M-Q}_n\text{-Z-T-(A-R}^1\text{R}^2\text{R}^3)_m \quad (I)$$

or

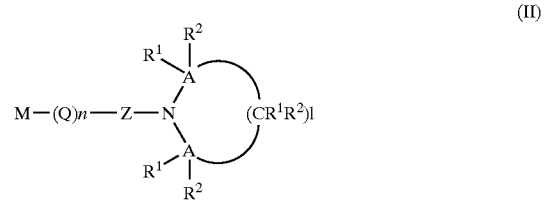
(II)

wherein M, Q, Z, T, A, $R^1$, $R^2$, $R^3$, l, m, and n have the meanings ascribed above. This provides an intermediate living polymer of the formula:

$$\text{M-P}_x\text{-Q}_n\text{-Z-T-(A-R}^1\text{R}^2\text{R}^3)_m$$

or

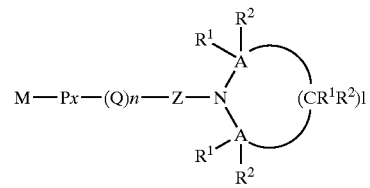

wherein:

P is a saturated hydrocarbyl group derived by incorporation of a compound selected from the group consisting of conjugated diene hydrocarbons, alkenylsubstituted aromatic compounds, and mixtures thereof;

x is an integer from 10 to 10,000; and

M, Q, Z, T, A, $R^1$, $R^2$, $R^3$, l, m, and n have the meanings ascribed above.

The intermediate living polymer can then be reacted with a suitable protonating, functionalizing, or coupling or linking agent, as known in the art. In one aspect of the invention, the living polymer is reacted with a functionalizing agent (or electrophile) of the formula:

$$\text{X-Y-T'-(A'-R}^4\text{R}^5\text{R}^6)_k$$

wherein:

X is halide, advantageously selected from the group consisting of chloride, bromide and iodide;

Y is a branched or straight chain hydrocarbon connecting group which contains 1–25 carbon atoms, optionally substituted with aryl or substituted aryl;

T' is selected from the group consisting of oxygen, sulfur, and nitrogen and mixtures thereof;

A' is an element selected from Group IVa of the Periodic Table of the Elements;

$R^4$, $R^5$, and $R^6$ are each independently selected from the group consisting of hydrogen, alkyl, substituted alkyl, aryl, substituted aryl, cycloalkyl, and substituted cycloalkyl, or $R^6$ is optionally a —$(CR^7R^8)_1$— group linking two A' when k is 2, wherein $R^7$ and $R^8$ are each independently selected from the group consisting of hydrogen, alkyl, substituted alkyl, aryl, substituted aryl, cycloalkyl, and substituted cycloalkyl, and l is an integer from 1 to 7; and k is 1 when T' is oxygen or sulfur, and 2 when T' is nitrogen. Thus the skilled artisan will appreciate that $R^6$ as used herein includes the group

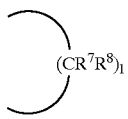

linking two A' groups when k is 2.

The functionalizing agents can be prepared as described, for example, in International Publication WO 97/16465, the entire disclosure of which is incorporated by reference. In addition, the electrophiles can be prepared as described in K. Ueda, A. Hirao, and S. Nakahama, Macromolecules, 23, 939 (1990); U.S. Pat. No. 5,496,940; U.S. Pat. No. 5,600,021; U.S. Pat. No. 5,362,699; A. Alexakis, M. Gardette, and S. Colin, Tetrahedron Letters, 29, 1988, 2951; B. Figadere, X. Franck, and A. Cave, Tetrahedron Letters, 34, 1993, 5893; J. Almena, F. Foubelo, and M. Yus, Tetrahedron, 51, 1995, 11883; D. F. Taber and Y. Wang, J. Org. Chem., 58, 1993, 6470; F. D. Toste and I. W. J. Still, Synlett, 1995, 159; and U.S. Pat. No. 5,493,044. The functionalization step can be conducted at temperatures ranging from about −30° C. to about 150° C.

Other compounds useful in functionalizing living polymers include, but are not limited to, alkylene oxides, such as ethylene oxide, propylene oxide, styrene oxide, and oxetane; oxygen; sulfur; carbon dioxide; halogens such as chlorine, bromine and iodine; propargyl halides; alkenylhalosilanes and omega-alkenylarylhalosilanes, such as styrenyldimethyl chlorosilane; sulfonated compounds, such as 1,3-propane sultone; amides, including cyclic amides, such as caprolactam, N-benzylidene trimethylsilylamide, and dimethyl formamide; silicon acetals; 1,5-diazabicyclo[3.1.0] hexane; allyl halides, such as allyl bromide and allyl chloride; methacryloyl chloride; amines, including primary, secondary, tertiary and cyclic amines, such as 3-(dimethylamino)-propyl chloride and N-(benzylidene) trimethylsilylamine; haloalkyltrialkoxysilanes; epihalohydrins, such as epichlorohydrin, epibromohydrin, and epiiodohydrin, and other materials as known in the art to be useful for terminating or end capping polymers. These and other useful functionalizing agents are described, for example, in U.S. Pat. Nos. 3,786,116 and 4,409,357, the entire disclosure of each of which is incorporated herein by reference.

Examples of difunctional coupling agents useful to form protected telechelic polymers include, but are not limited to, $Me_2SiCl_2$, $Me_2Si(OMe)_2$, $Me_2SnCl_2$, $Ph_2SiCl_2$, $MePhSiCl_2$, $ClMe_2SiCH_2CH_2SiMe_2Cl$, and $Me_2SiBr_2$, and the like and mixtures thereof.

Examples of useful multifunctional linking or coupling agents include isomeric (mixtures of ortho, meta and para) dialkenylaryls and isomeric di- and trivinylaryls, such as 1,2-dvinylbenzene, 1,3-divinylbenzene, 1,4-divinylbenzene, 1,2,4-trivinylbenzenes, 1,3-divinylnaphthalenes, 1,8-divinylnaphthalene, 1,2-diisopropenylbenzene, 1,3-diisopropenylbenzene, 1,4-diisopropenylbenzene, 1,3,5-trivinylnaphthalene, and other suitable materials known in the art to be useful for coupling polymers, as well as mixtures of coupling agents. Other exemplary multifunctional linking or coupling agents include halosilanes, halostannanes, phosphorus halides, and the like and mixtures thereof. Examples of the same include without limitation tin tetrachloride ($SnCl_4$), silicon tetrachloride ($SiCl_4$), methyl trichlorosilane ($MeSiCl_3$), $HSi(OMe)_3$, $Si(OEt)_4$, $Cl_3SiSiCl_3$, phosphorus trichloride and the like and mixtures thereof. See also U.S. Pat. Nos. 3,639,517 and 5,489,649, and R. P. Zelinski et al in J.Polym.Sci., A3, 93, (1965) for these and additional coupling agents. Mixtures of coupling agents can also be used. Generally, the amount of coupling agent used is such that the molar ratio of protected living polymer anions to coupling agents ranges from 1:1 to 24:1. This linking process is described, for example, in U.S. Pat. No. 4,409,357 and by L. J. Fetters in Macromolecules, 9,732 (1976).

The resultant polymer thus can be a linear, homotelechelic, heterotelechelic, branched, or radial polymer having one or more terminal functional groups. The polymer can be recovered from the reaction media and optionally hydrogenated and/or deprotected.

If a mixture of monomers is employed in the polymerization, the monomers can be added together to afford random or tapered block copolymers. The monomers can also be charged to the reactor sequentially to afford block copolymers.

Monomer(s) to be anionically polymerized to form living polymer anions can be selected from any suitable monomer capable of anionic polymerization, including conjugated alkadienes, alkenylsubstituted aromatic hydrocarbons, and mixtures thereof. Examples of suitable conjugated alkadienes include, but are not limited to, 1,3-butadiene, isoprene, 2,3-dimethyl-1,3-butadiene, 1,3-pentadiene, myrcene, 2-methyl-3-ethyl-1,3-butadiene, 2-methyl-3-ethyl-1,3-pentadiene, 1,3-hexadiene, 2-methyl-1,3-hexadiene, 1,3-heptadiene, 3-methyl-1,3-heptadiene, 1,3-octadiene, 3-butyl-1,3-octadiene, 3,4-dimethyl-1,3-hexadiene, 3-n-propyl-1,3-pentadiene, 4,5-diethyl-1,3-octadiene, 2,4-diethyl-1,3-butadiene, 2,3-di-n-propyl-1,3-butadiene, and 2-methyl-3-isopropyl-1,3-butadiene.

Examples of polymerizable alkenylsubstituted aromatic hydrocarbons include, but are not limited to, styrene, alpha-methylstyrene, vinyltoluene, 2-vinylpyridine, 4-vinylpyridine, 1-vinylnaphthalene, 2-vinylnaphthalene, 1-alpha-methylvinylnaphthalene, 2-alpha-methylvinylnaphthalene, 1,2-diphenyl-4-methyl-1-hexene and mixtures of these, as well as alkyl, cycloalkyl, aryl, alkylaryl and arylalkyl derivatives thereof in which the total number of carbon atoms in the combined hydrocarbon constituents is generally not greater than 18. Examples of these latter compounds include 3-methylstyrene, 3,5-diethylstyrene, 4-tert-butylstyrene, 2-ethyl-4-benzylstyrene, 4phenylstyrene, 4-p-tolylstyrene, 2,4-divinyltoluene and 4,5-dimethyl-1-vinylnaphthalene. U.S. Pat. No. 3,377,404, incorporated herein by reference in its entirety, discloses suitable additional alkenylsubstituted aromatic compounds.

Polar solvents (modifiers) can be added to the polymerization reaction to alter the microstructure of the resulting polymer, i.e., increase the proportion of 1,2 (vinyl) microstructure or to promote functionalization or randomization. Examples of polar modifiers include, but are not limited to, diethyl ether, dibutyl ether, tetrahydrofuran, 2-methyltetrahydrofuran, methyl tert-butyl ether, 1,2-dimethoxyethane (glyme), 1,2-diethoxyethane, diazabicyclo [2.2.2]octane, triethylamine, tributylamine, N-methylpiperidine, N-methylpyrrolidine, N,N,N',N'-tetramethylethylene diamine (TMEDA), and the like and mixtures thereof. The amount of the polar modifier added depends on the vinyl content desired, the nature of the monomer, the temperature of the polymerization, and the identity of the polar modifier. The polar solvent (modifier) can be added to the reaction medium at the beginning of the polymerization as part of the solvent reaction medium, added during the polymerization or after polymerization but prior to functionalization or coupling.

The polymers produced may be optionally hydrogenated to afford additional novel, functionalized polymers.

Examples of methods to hydrogenate the polymers of this invention are described in Falk, *Journal of Polymer Science: Part A-I*, vol. 9, 2617–2623 (1971), Falk, *Die Angewandte Chemie*, 21, 17–23 (1972), U.S. Pat. Nos. 4,970,254, 5,166, 277, 5,393,843, 5,496,898, and 5,717,035. The hydrogenation of the functionalized polymer is conducted in situ, or in a suitable solvent, such as hexane, cyclohexane or heptane. This solution is contacted with hydrogen gas in the presence of a catalyst, such as a nickel catalyst. The hydrogenation is typically performed at temperatures from 25° C. to 150° C., with a archetypal hydrogen pressure of 15 psig to 1000 psig. The progress of this hydrogenation can be monitored by InfraRed (IR) spectroscopy or Nuclear Magnetic Resonance (NMR) spectroscopy. The hydrogenation reaction is conducted until at least 90% of the aliphatic unsaturation has been saturated. The hydrogenated functional polymer is then recovered by conventional procedures, such as removal of the catalyst with aqueous acid wash, followed by solvent removal or precipitation of the polymer.

The protecting group can be removed from the functionalized polymer, if desired. Various methods can be employed for the removal of the protecting group. This deprotection can be conducted either prior to or subsequent to the optional hydrogentation of the aliphatic unsaturation. Deprotection of these polymers affords a linear or radial polymer which contain either a mono-, di- or multi-functional group. For example, to remove tert-alkyl-protected groups, the protected polymer is mixed with Amberlyst® 15 ion exchange resin and heated at an elevated temperature, for example 150° C., until deprotection is complete. In addition, tert-alkyl-protected groups can also be removed by reaction of the silicone polymer with trifluoroacetic acid, or trimethylsilyliodide. Additional methods of deprotection of the tert-alkyl protecting groups can be found in T. W. Greene and P. G. M. Wuts, Protective Groups in Organic Synthesis, Second Edition, Wiley, New York, 1991, page 41. The tert-butyldimethylsilyl protecting groups can be removed by treatment of the polymer with acid, such as hydrochloric acid, acetic acid, paratoluenesulfonic acid, or Dowex® 50W-X8. Additional methods of deprotection of the tert-butyldimethylsilyl protecting groups can be found in T. W. Greene and P. G. M. Wuts, Protective Groups in Organic Synthesis, Second Edition, Wiley, New York, 1991, pages 80–83.

In another aspect of this invention, unique polymers produced by the process described above are provided. The polymers produced by this process may have linear, branched or radial architecture. Further, the polymers may be monofunctional (produced by quench of the living anion), homotelechelic (for example produced by coupling of the living anion with a coupling agent with two active sites, such as dichlorodimethylsilane, heterotelechelic (produced by quench of the living polymer anion with an electrophile), or polyfunctional (produced by coupling of the living anion with a coupling agent with more than two active sites, such as tin tetrachloride or diisopropenylbenzene). The telechelic polymers can have two or more protected functional groups, in which the protecting group(s) and/or protected functionalities can be the same or different. Polymers possessing similarly protected functional groups can be deprotected by selecting a reagent specifically suited to remove the similar protecting groups. Alternatively, polymers possessing at least one free telechelically functional group and at least one protected telechelically functional group can also be prepared. In this aspect of the invention, one type of protecting group is selectively deprotected from a dissimilarly protected functionality on the end(s) of the polymer chains, produced as described above, using selective reagents specifically suited to remove the targeted protective group and liberate the desired functionality, on the end of the polymer chain.

The following table details experimental conditions that will selectively remove one of the protecting groups (more labile) from the polymer, while retaining the other protecting group (more stable).

| LABILE | STABLE | CONDITIONS |
|---|---|---|
| t-Butyldimethylsilyl | T-Butyl | Tetrabutylammonium fluoride |
| t-Butyldimethylsilyl | T-Butyl | 1 N HCl |
| t-Butyldimethylsilyl | Dialkylamino | Tetrabutylammonium fluoride |
| t-Butyldimethylsilyl | Dialkylamino | 1 N HCl |
| t-Butyl | Dialkylamino | Amberlyst ® resin |
| t-Amyl | Dialkylamino | Amberlyst ® resin |
| Trimethylsilyl | T-Butyl | Tetrabutylammonium fluoride |
| Trimethylsilyl | t-Butyl | 1 N HCl |
| Trimethylsilyl | Dialkylamino | Tetrabutylammonium fluoride |
| Trimethylsilyl | Dialkylamino | 1 N HCl |
| 2,2,5,5-Tetramethyl-2,5-disila-1-azacyclopentane | T-Butyl | Tetrabutylammonium Fluoride |
| 2,2,5,5-Tetramethyl-2,5-disila-1-azacyclopentane | T-Butyl | 1 N HCl |
| 2,2,5,5-Tetramethyl-2,5-disila-1-azacyclopentane | Dialkylamino | Tetrabutylammonium Fluoride |
| 2,2,5,5-Tetramethyl-2,5-disila-1-azacyclopentane | Dialkylamino | 1 N HCl |

Exemplary monofunctional and telechelic polymers of the invention are represented by the formulas below:

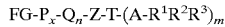

or

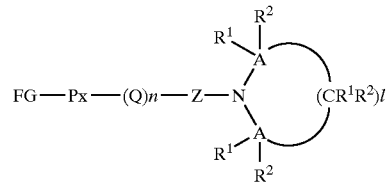

wherein:

FG is H or a protected or non-protected functional group;

P is a saturated hydrocarbyl group derived by incorporation of a compound selected from the group consisting of conjugated diene hydrocarbons, alkenylsubstituted aromatic compounds, and mixtures thereof;

x is an integer from 10 to 10,000; and

Q, n, Z, A, $R^1$, $R^2$, $R^3$, m, and l are the same as defined above.

The skilled artisan will appreciate that monofunctional polymers result when FG is hydrogen, produced by quench of the living anion. Telechelic polymers (both homotelechelic and heterotelechelic) can be prepared by reaction of the living polymer with any of the types of functionalizing agents or electrophiles as known in the art described in more detail above. For example, homotelechelic polymers can be produced by trapping of the living polymer anion with a protected, functionalized electrophile. Heterotelechelic polymers include those polymers in which FG and the protected functionality are different. In one aspect of the invention, heterotelechelic polymers include polymers which have been terminated using a functionalizing agent (or electrophile) of the formula X-Y-T'-(A'-$R^4R^5R^6$)$_k$ wherein X, Y, T', A', $R^4$, $R^5$, $R^6$ and k are the same as defined above. Exemplary polymers functionalized with such an electrophile can have the structure below:

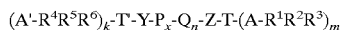

and

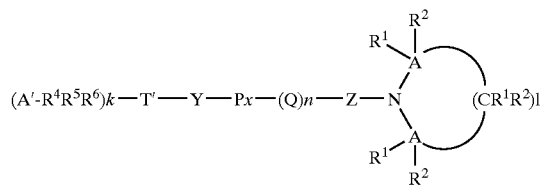

wherein:

Y, Z, T, T', A, A', P, Q, x, n, $R^1$, $R^2$, $R^3$, $R^4$, $R^5$, $R^6$, l, m and k are the same ascribed above (i.e., FG is -Y-T'-(A'-$R^4R^5R^6$)k).

The protected linear functionalized polymers can be treated to remove one or two protecting groups as described above.

As discussed above, the newly liberated functional groups can then participate in subsequent polymerization chemistry. For example, when the living chain end is reacted with a protected functionalized electrophile, the resultant protected functionality can also be deprotected, and the liberated functionality can optionally be reacted with one or more comonomers to polymerize a functional end thereof. Exemplary comonomers include without limitation cyclic ethers, diamines, diisocyanates, polyisocyanates, di-, poly- and cyclic amides, di- and polycarboxylic acids, diols, polyols, anhydrides, and the like and mixtures thereof. For example, functionalized polymers can be further reacted with monofunctional monomers, such as caprolactam, or other lactams, to form a polyamide block polymer segment, or cyclic ethers such ethylene oxide to form polyether blocks; or with difunctional monomers, such as diacids or anhydrides and diamines to form polyamide blocks, or diacids or anhydrides or lactones and diols to form polyester blocks, or diols and polyols with diisocyanates or polyisocyanates to form polyurethane blocks. Polyisocyanates or polyfunctional polyols are examples of polyfunctional monomers.

The functional group may also be reacted with a suitable agent containing a reactive olefin bond, such as a styrenic or acrylic functionality, including but not limited to acryloyl or methacryloyl chloride, which will act to change the nature of the functionality and provide a macromonomer having additional olefin end groups that are capable of polymerizing with other free radically polymerizable monomers.

In yet another aspect of the invention, two or more living polymers can be linked using a coupling or linking agent as known in the art. In one embodiment of this aspect of the invention, the linking agent is a difunctional linking agent. The resultant homotelechelic polymer is represented by the below formulas:

L-[P$_x$-Q$_n$-Z-T-(A-$R^1R^2R^3$)$_m$]$_2$ and

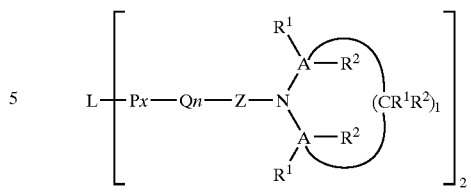

wherein:
 $R^1$, $R^2$, $R^3$, P, Q, Z, A, x, l, m and n have the meanings ascribed above; and
 L is a residue of a difunctional linking agent, such as SiMe$_2$ residue derived form the difunctional linking agent SiMe$_2$Cl$_2$.

In another embodiment of this aspect of the invention, the linking agent is a multifunctional linking agent. The resultant star or multi-branched polymer is represented by the below formulas:

L'-[P$_x$-Q$_n$-Z-T-(A-$R^1R^2R^3$)$_m$]$_v$ or

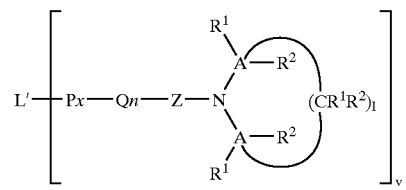

wherein:
 $R^1$, $R^2$, $R_3$, P, Q, Z, A, x, l, m, and n have the meanings ascribed above;
 L' is a residue of a multifunctional linking agent, such as divinylbenzene; and
 v is from 3 to 30. As the skilled artisan will appreciate, each $R^1$, $R^2$, $R^3$, P, Q, Z, A, x, l, m, and n can differ if the coupled living polymers are prepared using different protected functionalized and/or non-functional initiators.

These homotelechelic and star or multi-branched polymers can be hydrogenated, deprotected and/or further reacted with one or more comonomers to form polymer segments, each as discussed above.

The polymers can thus include what can be referred to generally as two polymer segments. One segment can be defined as "P" and is the primary polymer chain resulting from polymerization of the selected monomers. The other polymer segment can be defined as "Q" and results from incorporation of the chain extension "Q" of the protected functionalized initiators as described herein. Still further, the polymer segments P and Q may not both be the same homopolymers. For example, in one aspect of the invention, both P and Q are not both polybutadiene polymer segments, or P and Q are not both polystyrene polymer segments, etc.

Thus the invention includes polymers which include a primary polymer chain "P" resulting from polymerization of dienes, alkenylsubstituted aromatics, or mixtures thereof, and a less than one 1 equivalent unit terminal segment "Q" resulting from incorporation of the chain extension Q of the initiators, which also can include dienes, alkenylsubstitued aromatics, and mixtures thereof. Various embodiments of the invention can include: polymers wherein P is a homopolymer segment derived by incorporation of a conjugated diene hydrocarbon and Q is a homopolymer segment derived by incorporation of a different diene hydrocarbon; polymers wherein P is a homopolymer segment derived by incorporation an alkenylsubstituted aromatic hydrocarbon and Q is a homopolymer segment derived by incorporation of a different alkenylsubstituted aromatic hydrocarbon; polymers wherein one of P and Q is a homopolymer segment derived by incorporation a conjugated diene and the other of P and Q is a homopolymer segment derived by incorporation of an alkenylsubstituted aromatic hydrocarbon; polymers wherein P is a copolymer segment and Q is a homopolymer segment; polymers wherein P is a homopolymer segment and Q is a copolymer segment; and polymers wherein each of P and Q are different copolymer segments. Still further, each of P and Q can be homopolymer segments derived by incorporation of the same monomer(s) but with different microstructures. For example, P or Q can have a predominately 1,4 microstructure and the other of P or Q have a predominately 1,2 microstructure, by adding THF or other suitable polar modifier during synthesis.

The chain extended initiators used in accordance with the present invention provide many advantages. For example, the chain extension provides increased hydrocarbon solubility as compared to non-chain extended compounds. In addition, the chain extension provides flexibility in the synthesis of polymers having various structures. In this regard, the polymers of the invention can be broadly referred to as "copolymers." However, the "copolymers" of the claimed invention differ structurally from conventional copolymers, and prior to this invention, one skilled in the art could not tailor a copolymer structure with the specificity provided by this invention.

Specifically, conventional copolymers include random copolymers comprising different monomer units, such as a mixture of butadiene and styrene units. Conventional copolymers also include block copolymers including discrete blocks of polymer segments, for example polybutadiene blocks alternating with polystyrene blocks.

In contrast to conventional copolymer structures, however, in the present invention, polymers can be synthesized having a specific compositional make-up. In particular, as discussed above, both the primary chain P and the polymer segment Q adjacent thereto can be tailored. Thus, for example, copolymers can be prepared which include a homopolymer as the primary polymer component with a less than 1 equivalent polymer block Q at one end thereof comprising a different homopolymer or a copolymer segment. Alternatively, the copolymers can include a copolymer as the primary polymer chain with a less than one equivalent unit block Q at one end thereof comprising a homopolymer or a different copolymer segment. Thus in accordance with the present invention copolymer structure can be tailored to provide a copolymer which includes a less than 1 equivalent unit Q which differs compositionally from the primary polymer chain.

Thus the molecular architecture of compounds of the present invention can be precisely controlled. The degree of functionality can be adjusted by simply varying the ratio of functional initiator to coupling agent. Further, the monomer identity, the monomer composition and molecular weight can be independently manipulated by varying the monomer charged. Finally, the number of polymer arms can be adjusted by varying the nature of the coupling agent, and the ratio of living polymer to the coupling agent.

The present invention will be further illustrated by the following non-limiting examples.

EXAMPLE 1

Preparation of 3-(Hexamethyleneimino)-1-Propyllithium

Chain Extended with 0.13 Equivalents of Isoprene

A one liter Wheaton bottle was fitted with a magnetic stir bar, and a rubber septum equipped with a thermocouple and an argon inlet. This apparatus was dried in an oven overnight at 125° C., assembled hot, and allowed to cool to room temperature in a stream of argon. 3-(Hexamethyleneimino)-1-propyllithium, 534.1 grams (0.3445 moles) was weighed into the bottle. This material was a heavy slurry. The magnetic stirrer was started. The temperature was slowly raised to 60–65° C. with a heat gun to promote the chain extension reaction. After five minutes at this temperature, all the solids had dissolved. Isoprene, 3.15 grams (0.0462 mole, 0.134 equivalents) was then added with a syringe. The reaction temperature was then controlled with a cooling bath at 60–65° C. The reaction mixture was held at this temperature for thirty minutes, then allowed to cool to room temperature. This afforded an amber solution, yield=537 grams.

Active Base=9.446 wt. % (0.642 moles/kg).

Yield (based on active C-Li)=99.7%.

After storage overnight at 15° C., no solids had precipitated. The sample bottle was placed in a refrigerator at −1° C. for twenty-four hours. No solids had precipitated.

EXAMPLE 2

Preparation of 3-(Hexamethyleneimino)-1-Propyllithium

Chain Extended with 0.51 Equivalents of Isoprene

A one-liter Wheaton bottle was fitted with a magnetic stir bar, and a rubber septum equipped with a thermocouple and an argon inlet. This apparatus was dried in an oven overnight at 125° C., assembled hot, and allowed to cool to room temperature in a stream of argon. 3-(Hexamethyleneimino)-1-propyllithium, 463.8 grams (10.27 wt. %, 0.3236 moles) was weighed into the bottle. This material was a heavy slurry. The magnetic stirrer was started. Isoprene, 11.25 grams, (0.1651 mole, 0.51 equivalents) was then added with a syringe. The temperature was slowly raised to 60–65° C. with a heat gun to promote the chain extension reaction. After five minutes at this temperature, all the solids had dissolved. The reaction temperature was then controlled with a cooling bath at 60–65° C. The reaction mixture was held at this temperature for thirty minutes, then allowed to cool to room temperature. This afforded an amber solution, yield=473.28 grams.

Active Base=10.03 wt. % (0.6814 moles/kg).

Yield (based on active C-Li)=99.7%.

After storage overnight at 15° C., no solids had precipitated. The sample bottle was placed in a refrigerator at −1° C. for twenty-four hours. No solids had precipitated. This solution was transferred to a dry, one-liter pear shaped flask. A majority of the solvent was removed on the rotary evaporator, at full vacuum, with a bath temperature of 40° C. This afforded a dark amber oil, yield=154.85 grams.

Active Base=30.65 wt. % (2.083 moles/kg).

This solution was stored at −1° C. for one week, and no precipitate was observed.

EXAMPLE 3

Preparation of 3-(Hexamethyleneimino)-1-Propyllithium

Chain Extended with 0.90 Equivalents of Isoprene

A 500 ml. four-necked Morton flask was equipped with a mechanical stirrer, a Claisen adapter with an dry ice condenser, a thermocouple, and a 250 milliliter pressure-equalizing dropping funnel fitted with an argon inlet. This apparatus was dried in an oven overnight at 125° C., assembled hot, and allowed to cool to room temperature in a stream of argon. Lithium metal dispersion was washed free of mineral oil with hexane (2×100 ml), and pentane (1×100 ml). The resultant lithium dispersion was dried in a stream of argon, weighed (14.71 grams, 2.119 moles, 3.333 equivalents), and transferred to the reaction flask. Twenty milliliters of 0.29 Molar (0.0058 mole, 0.0091 equivalents) of 3-(hexamethyleneimino)-1-propyllithium was added as a lithium metal conditioner. The reaction mixture was stirred at ambient temperature for twenty five minutes. Cyclohexane was then added, 196.0 grams. The mechanical stirrer was set at an agitation rate of 880 RPMs. The reaction mixture was heated to 67° C. with a heating mantle. The heat source was removed. The dropping funnel was charged with 115.35 grams of 96.49 wt. % (0.6354 moles, 1.00 equivalent) of 1-chloro-3-(hexamethyleneimino)-propane. The precursor was added dropwise, at an approximate rate of 1.5 ml/min. An exotherm was noted after 1.3% of the feed mixture had been added. The reaction mixture was maintained at 62–64° C. with a hexane cooling bath. The total halide feed time was 87 minutes. The temperature of the reaction mixture fell off rapidly after the halide feed was completed. After fifteen minutes, the stirrer speed was decreased to 400 RPMs. The reaction mixture was allowed to stir for an additional 1.75 hours, and then reheated to a temperature of 67° C. with a heating mantle. Then isoprene, 38.90 grams (0.571 moles, 0.899 equivalents) was added at a feed rate of approximately 2.0 ml/min. The temperature was maintained at 64–66° C. during the feed. The reaction mixture was allowed to cool to room temperature then to stir for an additional hour at 400 RPMs. The reaction mixture was then transferred at 40° C. into a medium porosity pressure filter. Rapid filtration was observed. The lithium muds were washed with cyclohexane (3×25 ml.). This afforded an amber solution, 401.03 grams.

Active Base=21.81 wt. % (1.482 moles/kg).

Yield (based on active C-Li)=92.6% corrected for the conditioner added.

After storage overnight at 15° C., no solids had precipitated. The sample bottle was placed in a refrigerator at −1° C. for twenty-four hours. No solids had precipitated. This solution was transferred to a dry, one liter pear shaped flask. A majority of the solvent was removed on the rotary evaporator, at full vacuum, with a bath temperature of 40° C. This afforded a dark amber oil, yield=230.07 grams.

Active Base=35.74 wt. % (2.428 moles/kg).

This solution was stored at −1° C. in a refrigerator for ten days, and no precipitate was observed.

COMPARATIVE EXAMPLE

Preparation of 3-(Hexamethyleneimino)-1-Propyllithium—No Chain Extension

A 500 ml. four-necked Morton flask was equipped with a mechanical stirrer, a Claisen adapter with an dry ice condenser, a thermocouple, and a 250 milliliter pressure-equalizing dropping funnel fitted with an argon inlet. This apparatus was dried in an oven overnight at 125° C., assembled hot, and allowed to cool to room temperature in a stream of argon. Lithium metal dispersion was washed free of mineral oil with hexane (2×100 ml), and pentane (1×100 ml). The resultant lithium dispersion was dried in a stream of argon, weighed (7.76 grams, 1.118 moles, 4.21 equivalents), and transferred to the reaction flask with 330.27 grams of cyclohexane. The mechanical stirrer was set at an agitation rate of 500 RPMs. Ten milliliters of 0.29 Molar (0.0029 mole, 0.0109 equivalents) of 3-(hexamethyleneimino)-1-propyllithium was added as a lithium metal conditioner. The reaction mixture was stirred at ambient temperature for fifty minutes, and then the reaction mixture was heated to 70° C. with a heating mantle. The heat source was removed and the speed was increased to 780 RPMS. The dropping funnel was charged with 103.37 grams of 45.2 wt. % (0.2659 moles, 1.00 equivalent) of 1-chloro-3-(hexamethyleneimino)-propane. The precursor was added dropwise, at an approximate rate of 2.00 ml/min. An exotherm was noted after 12% of the feed mixture had been added. The reaction mixture was maintained at 64–68° C. with a hexane cooling bath. The total halide feed time was 58 minutes. The addition funnel was rinsed with cyclohexane (2×10 ml.). The temperature of the reaction mixture fell off rapidly after the halide feed was completed. After one hour, the stirrer speed was decreased to 300 RPMs. After an additional hour stirring, the reaction mixture was transferred at 31° C. to a medium porosity pressure filter. The lithium muds were washed with cyclohexane (3×50 ml). This afforded a slightly hazy, pale yellow solution, 552.50 grams.

Active Base=6.707 wt. % (0.4556 moles/kg).

Yield (based on active C-Li)=93.5% corrected for the conditioner added.

This solution formed a heavy white precipitate after storage overnight at −5° C. in the refrigerator.

EXAMPLE 4

Preparation of 3-(Pyrrolidino)-1-Propyllithium

Chain Extended with 0.12 Equivalents of Isoprene

A 1000 ml. four-necked Morton flask was equipped with a mechanical stirrer, a Claisen adapter with an dry ice condenser, a thermocouple, and a 250 milliliter pressure-equalizing dropping funnel fitted with an argon inlet. This apparatus was dried in an oven overnight at 125° C., assembled hot, and allowed to cool to room temperature in a stream of argon. Lithium metal dispersion was washed free of mineral oil with hexane (2×100 ml), and pentane (1×100 ml). The resultant lithium dispersion was dried in a stream of argon, weighed (17.17 grams, 2.48 moles, 2.67 equivalents), and transferred to the reaction flask. Cyclohexane was then added, 495.6 grams (600 ml.). Ten milliliters of 0.65 Molar (0.0065 mole, 0.007 equivalents) of 3-(pyrrolidino)-1-propyllithium was added as a lithium metal conditioner. The reaction mixture was stirred at ambient temperature for 2.5 hours. The mechanical stirrer was set at an agitation rate of 710 RPMs. The reaction mixture was heated to 65° C. with a heating mantle. The heat source was removed. The dropping funnel was charged with 141.00 grams of 97.0 wt. % (0.9263 moles, 1.00 equivalent) of 1-chloro-3-(pyrrolidino)-propane. The precursor was added dropwise, at an approximate rate of 4.2 ml/min. An exotherm was noted after 2.7% of the halide feed had been added. The reaction mixture was maintained at 62–64° C. with a hexane cooling bath. The total halide feed time was 43 minutes. The temperature of the reaction mixture fell off rapidly after the halide feed was completed. After twenty-five minutes, the stirrer speed was decreased to 200 RPMs. The reaction mixture was reheated to a temperature of 61° C. with a heating mantle. The reaction mixture was then transferred at 60° C. into a medium porosity pressure filter. Rapid filtration was observed. The lithium muds were washed with hot cyclohexane (3×50 ml.). This afforded a hazy yellow solution, 756.78 grams.

Active Base=14.63 wt. % (1.228 moles/kg).

Yield (based on active C-Li)=99.4% corrected for the conditioner added.

After storage overnight at 20° C., a heavy white precipitate had formed.

A 250 ml. Wheaton bottle was fitted with a magnetic stir bar, and a rubber septum equipped with a thermocouple and an argon inlet. This apparatus was dried in an oven overnight at 125° C., assembled hot, and allowed to cool to room temperature in a stream of argon. A warm solution of 3-(pyrrolidino)-1-propyllithium, 181.45 grams (0.2228 moles) was weighed into the bottle. This material was a heavy slurry at room temperature. The magnetic stirrer was started. The temperature was slowly raised to 60–65° C. with a heat gun to promote the chain extension reaction. Isoprene, 1.75 gams (0.0257 mole, 0.115 equivalents) was then added with a syringe. The reaction temperature was then controlled with a cooling bath at 60–65° C. The reaction mixture was held at this temperature for thirty minutes, then allowed to cool to room temperature. This afforded an amber solution. The sample was diluted with heptane, 33.07 grams, to prevent the cyclohexane from freezing.

Active Base=9.53 wt. %.

Yield (based on active C-Li)=99.8%.

The sample bottle was placed in a refrigerator at −2° C. for forty-eight hours. No solids had precipitated.

EXAMPLE 5

Preparation of 3-(Pyrrolidino)-1-Propyllithium

Chain Extended with 0.52 Equivalents of Isoprene

A 250 ml. Wheaton bottle was fitted with a magnetic stir bar, and a rubber septum equipped with a thermocouple and an argon inlet. This apparatus was dried in an oven overnight at 125° C., assembled hot, and allowed to cool to room temperature in a stream of argon. 3-(Pyrrolidino)-1-propyllithium, 185.15 grams (0.2274 moles) was weighed into the bottle. This material was a heavy slurry. The magnetic stirrer was started. The temperature was slowly raised to 60–65° C. with a heat gun to promote the chain extension reaction. Isoprene, 8.000 gams, (0.117 mole, 0.516 equivalents) was then added with a syringe. The reaction temperature was then controlled with a cooling bath at 60–65° C. The reaction mixture was held at this temperature for thirty minutes, then allowed to cool to room temperature. This afforded an amber solution, yield=193.15 grams.

Active Base=14.02 wt. %.

Yield (based on active C-Li)=99.7%.

After storage overnight at −2° C. in a refrigerator, no solids had precipitated. This solution was transferred to a dry, 500 ml., pear shaped flask. A majority of the solvent was removed on the rotary evaporator, at full vacuum, with a bath temperature of 40° C. This afforded a dark amber oil, yield=104.90 grams. Heptane, 6.11 grams, was added as a freezing point depressant.

Active Base=24.14 wt %.

This sample was placed in a refrigerator at −2° C. for four days and no solids had precipitated.

EXAMPLE 6

Preparation of 3-(Pyrrolidino)-1-Propyllithium

Chain Extended with 0.97 Equivalents of Isoprene

A 1000 ml. four-necked Morton flask was equipped with a mechanical stirrer, a Claisen adapter with an dry ice condenser, a thermocouple, and a 250 milliliter pressure-equalizing dropping funnel fitted with an argon inlet. This apparatus was dried in an oven overnight at 125° C., assembled hot, and allowed to cool to room temperature in a stream of argon. 3-(Pyrrolidino)-1-propyllithium, 370.79 grams of 14.63 wt. % (0.4554 moles) was transferred into the flask. This material was a heavy slurry. The mechanical stirrer was started at 250 RPMs. The temperature was slowly raised to 70° C. with a heating mantle to promote the chain extension reaction. Isoprene, 30.14 gains, (0.442 moles, 0.971 equivalents) was then charged to the addition funnel. The isoprene was added dropwise. The reaction temperature was then controlled with a cooling bath at 65–71° C. The reaction mixture was held at this temperature for thirty minutes, then allowed to cool to room temperature. This afforded an amber solution.

This solution was transferred to a dry, 1000 ml., pear shaped flask. A majority of the solvent was removed on the rotary evaporator, at full vacuum, with a bath temperature of 30° C. This afforded a mobile, orange oil, yield=228.07 grams.

Active Base=23.68 wt. %.

COMPARATIVE EXAMPLE

Preparation of 3-(Pyrrolidino)-1-Propyllithium—No Chain Extension

A 1000 ml. four-necked Morton flask was equipped with a mechanical stirrer, a Claisen adapter with an dry ice condenser, a thermocouple, and a 500 milliliter pressure-equalizing dropping funnel fitted with an argon inlet. This apparatus was dried in an oven overnight at 125° C., assembled hot, and allowed to cool to room temperature in a stream of argon. Lithium metal dispersion was washed free of mineral oil with hexane (2×100 ml), and pentane (1×100 ml). The resultant lithium dispersion was dried in a stream of argon, weighed (16.29 grams, 2.347 moles, 3.55 equivalents), and transferred to the reaction flask. Ten milliliters of 0.67 Molar (0.0067 mole, 0.0101 equivalents) of 3-(pyrrolidino)-1-propyllithium was added as a lithium metal conditioner. Cyclohexane, 329.0 grams, was then added The reaction mixture was stirred at ambient temperature for twenty minutes. The mechanical stirrer was set at an agitation rate of 830 RPMs. The reaction mixture was heated to 65° C. with a heating mantle. The heat source was removed. The dropping funnel was charged with 309.0 grams of 31.62 wt. % (0.6617 moles, 1.00 equivalent) of 1-chloro-3-(pyrrolidino)-propane. The precursor was added dropwise, at an approximate rate of 6.00 ml/min. An exotherm was noted after 3.95% of the feed mixture had been added. The reaction mixture was maintained at 62–65° C. with a hexane-cooling bath. The total halide feed time was 63 minutes. The addition funnel was rinsed with cyclohexane (2×10 ml.). The temperature of the reaction mixture fell off rapidly after the halide feed was completed. After ten minutes, the stirrer speed was decreased to 400 RPMs. After an additional hour stirring, the reaction mixture was transferred to a medium porosity pressure filter. The lithium muds were washed with cyclohexane (3×100 ml). This afforded a slightly hazy, pale tan suspension, 859.60 grams.

Active Base=9.167 wt. % (0.7697 moles/kg).

Yield (based on active C-Li)=98.9% corrected for the conditioner added.

Preparation of Precursor 1-Chloro-3-(1,1-dimethylethoxy)-propane

A three-necked, 3-liter Morton flask was equipped with a mechanical stirrer, a Claisen adapter, a thermocouple, a dry-ice condenser with a gas inlet, and a dip tube. The glassware was dried in an oven at 125° C. overnight, assembled hot, and purged under argon until cool. The reaction flask was then charged with Amberlyst® 15 resin (42.0 grams), 3-chloro-1-propanol (4.65 moles, 1 equivalent, 440.0 grams), and pentane (3.7 equivalents, 2000 mL). These reagents were stirred at 500 RPMs. The alcohol was not completely soluble in the organic solvent. A cylinder of 2-methylpropene was attached to the dip tube and 261.16 grams (4.65 moles, 1 equivalent) was fed into the reaction vessel. The feed rate was approximately 2 grams/min. As the conversion of starting alcohol material into product proceeded, the reaction mixture became one liquid phase. The formation of the product was monitored via Gas Chromatography. After all the starting material was consumed, the solution was then pumped into a pressure filter where the Amberlyst® resin catalyst was separated from the product. The resin was washed with fresh pentane (2×100 ml.). The product was purified by distillation from 20 grams of potassium carbonate through a twelve inch Vigreaux column, under reduced pressure. This afforded a clear, colorless oil, yield=598.82 grams (83.75%). Boiling Point=64° C. at 60 mm Hg. GC assay=0.00% 2-methylpropene, 0.81% pentane, 1.13% 3-chloro-1-propanol, and 98.06% desired product. NMR(CDCl3): 3.63 (t, J=6 Hz, 2H), 3.46 (t, J=6 Hz, 2H), 2.28–1.62 (m, 2H), and 1.21 (s, 9H) ppm.

EXAMPLE 7

Preparation of 3-(1,1-Dimethylethoxy)-1-propyllithium

Chain Extended with 0.50 Equivalents of Isoprene

A one-liter three-necked Morton flask was equipped with a mechanical stirrer, Claisen adapter with an ice condenser and gas inlet, and a 250 milliliter pressure-equalizing dropping funnel. This apparatus was dried in an oven overnight at 125° C., assembled hot, and allowed to cool to room temperature in a stream of argon. Lithium metal dispersion was washed free of mineral oil with hexane (2×100 ml), and pentane (1×100 ml). The resultant lithium dispersion was dried in a stream of argon, weighed (12.22 grams, 1.76 moles, 2.80 equivalents), and transferred to the reaction flask with 550 ml of cyclohexane. The mechanical stirrer was set at an agitation rate of 500 RPMs, and the reaction mixture was heated to 80° C. with a hearing mantle. The heat source was removed. The dropping funnel was charged with 94.90 grams (0.63 moles, 1.00 equivalent) of the precursor. The precursor was added dropwise, at an approximate rate of 1.59 ml/min. The reaction temperature was maintained at 70° C. with a dry ice/hexane bath. The total halide feed time was 66 minutes. The reaction mixture was allowed to stir for one hour post-feed and maintained at a temperature of 67.5° C. with a heating mantle. Then isoprene, 22.89 grams (0.63 moles, 0.50 equivalents of isoprene) was added at a feed rate of approximately 1.58 ml/min. The temperature was maintained at 62.5° C. during and after the feed. The reaction stirred for two hours before it was cooled to room temperature and filtered through a medium porosity pressure filter. The lithium muds were washed with cyclohexane (2×70 ml). The filtration took 15 minutes. This afforded a clear, light yellow solution, 513.07 g, 650 ml. The sample was stored in 0° C. refrigerator. This solution was transferred to a dry, 1000 ml pear-shaped flask. Some solvent was removed on the rotary evaporator, at full vacuum, with a bath temperature of 30° C. This afforded a light yellow solution, yield= 386.01 g, 550 ml. Crystals were present after one day.

Total base=23.2 wt. %

Active=21.1 wt. % (1.35 moles/kg)

Chloride=106 ppm

Yield (based on active C-Li)=83%

EXAMPLE 8

Preparation of 3-(1,1-Dimethylethoxy)-1-propyllithium

Chain Extended with 0.75 Equivalents of Isoprene

A one-liter three-necked Morton flask was equipped with a mechanical stirrer, Claisen adapter with an ice condenser and gas inlet, and a 250 milliliter pressure-equalizing dropping funnel. This apparatus was dried in an oven overnight at 125° C., assembled hot, and allowed to cool to room temperature in a stream of argon. Lithium metal dispersion was washed free of mineral oil with hexane (2×100 ml), and pentane (1×100 ml). The resultant lithium dispersion was dried in a stream of argon, weighed (12.83 grams, 1.85 moles, 2.80 equivalents), and transferred to the reaction flask with 400 ml of cyclohexane. The mechanical stirrer was set at an agitation rate of 500 RPMs, and the reaction mixture was heated to 80° C. The heat source was removed. The dropping funnel was charged with 99.88 grams (0.66 moles, 1.00 equivalent) of precursor. The precursor was added dropwise, at an approximate feed rate of 1.35 ml/min. The reaction temperature was maintained at 70° C. with a dry ice/hexane bath. The total halide feed time was 78 minutes. The reaction mixture was allowed to stir for one hour post-halide feed and maintained at a temperature of 67.5° C. with a heating mantle. Then isoprene, 37.65 grams (0.66 moles, 0.75 equivalents) was added at a feed rate of approximately 2.00 mL/min. The temperature was maintained at 62.5° C. after the feed. The reaction stirred for 2.5 hours before cooling to room temperature and filtering through a medium porosity pressure filter. The lithium muds were washed with cyclohexane (2×50 ml). The filtration took 10 minutes. This afforded a light yellow solution, 580.83 grams, 750 ml. The sample was stored in 0° C. refrigerator. This solution was transferred to a dry, 1000 ml pear-shaped flask. Some solvent was removed on the rotary evaporator, at full vacuum, with a bath temperature of 30° C. This afforded a light yellow solution, yield=320.79 grams, 500 ml.

Total base=33.5 wt. %

Active=29.8 wt. % (1.72 moles/kg)

Chloride=126 ppm.

Yield (based on active C-Li)=83.6%

EXAMPLE 9

Preparation of 3-(1,1-Dimethylethoxy)-1-propyllithium

Chain Extended with One Equivalent of Isoprene

A one-liter three-necked Morton flask was equipped with a mechanical stirrer, Claisen adapter fitted with a dry ice condenser and gas inlet, and a 250 milliliter pressure-equalizing dropping funnel. This apparatus was dried in an oven overnight at 125° C., assembled hot, and allowed to cool to room temperature in a stream of argon. Lithium metal dispersion was washed free of mineral oil with hexane (2×100 ml.) and pentane (1×100 ml.). The resultant lithium dispersion was dried in a stream of argon, weighed 11.24 grams (1.59 moles, 2.80 equivalents) and transferred to the reaction flask with 800 ml of cyclohexane. The mechanical stirrer was set at an agitation rate of 500 RPMs, and the reaction mixture was heated to 80° C. with a heating mantle. The heat source was removed. The dropping funnel was charged with 84.81 g (0.57 moles, 1.00 equivalent) of the precursor. The precursor was added dropwise, at an approximate feed rate of 1.46 ml/min. The reaction mixture was maintained at 70° C. with a dry ice/hexane bath. The total halide feed time was 65 minutes. The reaction was allowed to stir for an additional one hour and maintained at a temperature of 67.5° C. with a heating mantle. Then isoprene 38.89 grams (0.57 moles, 1.0 equivalents) was at an approximate feed rate of 2.00 ml/min. The temperature was maintained at 62.5° C. during the feed. The reaction mixture was then allowed to cool to room temperature. The reaction stirred for two hours before it was transferred to a medium porosity pressure filter. The lithium muds were washed with cyclohexane (2×50 ml). This afforded a yellow solution, 696.58 grams, 900 ml. The sample was stored in 0° C. refrigerator. This solution was transferred to a dry, 1000 ml pear-shaped flask. A majority of the solvent was removed on the rotary evaporator, at full vacuum, with a bath temperature of 30° C. This afforded a yellow solution, 256.85 grams, 425 ml.

Total base=40.1 wt. %.

Active base=35.0 wt. %. (1.84 moles/kg)

Chloride=110 ppm.

Yield (based on active C-Li)=83.5%.

EXAMPLE 10

Preparation of 3-(1,1-Dimethylethoxy)-1-propyllithium

Chain Extended with 2.0 Equivalents of Isoprene

A one-liter three-necked Morton flask was equipped with a mechanical stirrer, Claisen adapter with an ice condenser and gas inlet, and a 250 milliliter pressure-equalizing dropping funnel. This apparatus was dried in an oven overnight at 125° C., assembled hot, and allowed to cool to room temperature in a stream of argon. Lithium metal dispersion was washed free of mineral oil with hexane (2×100 ml) and pentane (1×100 ml). The resultant lithium dispersion was dried in a stream of argon, weighed (13.90 grams, 2.00 moles, 2.80 equivalents), and transferred to the reaction flask with 400 ml of cyclohexane. The mechanical stirrer was set at an agitation rate of 500 RPMs, and the reaction mixture was heated to 80° C. with a heating mantle. The heat source was removed. The dropping funnel was charged with 107.82 grams (0.72 moles, 1.00 equivalent) of the precursor. The precursor was added dropwise, at an approximate rate of 0.71 ml/min. The reaction temperature was maintained at 70° C. with a dry ice/hexane bath. The total halide feed time was 162 minutes. The reaction mixture was allowed to stir for one hour post-feed, and maintained at a temperature of 70° C. with a heating mantle. Then isoprene, 98.20 grams (0.72 moles, 2.00 equivalents of isoprene) was added at a feed rate of approximately 2.55 ml/min. The temperature was maintained at 62.5° C. during and after the feed. The reaction stirred for two hours before it was cooled to room temperature and filtered through a medium porosity pressure filter. The lithium muds were washed with cyclohexane (1×50 ml). The filtration took 15 minutes. This afforded a dark yellow solution, 647.08 grams, 850 ml. The sample was stored in 0° C. refrigerator. This solution was transferred to a dry, 1000 ml pear shaped flask. A majority of the solvent was removed on the rotary evaporator, at full vacuum, with a bath temperature of 30° C. This afforded a mobile, yellow oil, yield=307.92 g, 475 ml. Maximum solubility was observed when crystals were present after storage in 0° C. refrigerator.

Total base=56.1 wt. %

Active=49.4 wt. % (1.91 mole/kg)

Chloride=146 ppm

Yield=82%

COMPARATIVE EXAMPLE

Preparation of 3-(1,1-Dimethylethoxy)-1-propyllithium—No Chain Extension

A one-liter three-necked Morton flask was equipped with a mechanical stirrer, Claisen adapter with an ice condenser and gas inlet, and a 250 milliliter pressure-equalizing dropping funnel. This apparatus was dried in an oven overnight at 125° C., assembled hot, and allowed to cool to room temperature in a stream of argon. Lithium metal dispersion was washed free of mineral oil with hexane (2×100 ml), and pentane (1×100 ml). The resultant lithium dispersion was dried in a stream of argon, weighed (15.71 grams, 2.23 moles, 2.80 equivalents), and transferred to the reaction flask with 400 ml of cyclohexane. The mechanical stirrer was set at an agitation rate of 500 RPMs, and the reaction mixture was heated to 80° C. with a heating mantle. The heat source was removed. The dropping funnel was charged with 120.56 grams (0.80 moles, 1.00 equivalent) of the precursor. The precursor was added dropwise, at an approximate rate of 0.64 ml/min. The total halide feed time was 64 minutes. The reaction mixture was allowed to stir for an additional hour and 30 minutes, and maintained at a temperature of 70° C. with a heating mantle. The heat source was then removed and the reaction mixture was allowed to cool to room temperature before filtration. This particular reaction did not contain any equivalents of isoprene. The batch was filtered through a medium porosity pressure filter. The lithium muds were washed with cyclohexane (1×50 ml). Th filtration took 20 minutes. This afforded a clear, colorless solution, 421.02 grams, 550 ml. This sample was stored in a 0° C. refrigerator. Crystals were present after one day.

Total base=4.5 wt. %

Active=4.4 wt. % (0.36 moles/kg)

Chloride=116 ppm

Yield (based on active C-Li)=16.2%

EXAMPLE 11

Preparation of 2,2-Dimethyl-3-trimethylsiloxy-1-propyllithium

Chain Extended with 0.5 Equivalents of Isoprene

A 300 ml three-necked Morton flask was equipped with a mechanical stirrer, Claisen adapter fitted with a dry ice condenser and gas inlet, and a 125 milliliter pressure-equalizing dropping funnel. This apparatus was dried in an oven overnight at 125° C., assembled hot, and allowed to cool to room temperature in a stream of argon. Lithium metal dispersion was washed free of mineral oil with hexane (2×100 ml.) and pentane (1×100 ml.). The resultant lithium dispersion was dried in a stream of argon, weighed 5.72 grams (0.824 moles, 2.80 equivalents) and transferred to the reaction flask with 103 ml. of cyclohexane. The mechanical stirrer was set at an agitation rate of 500 RPMs, and the reaction mixture was heated to 70° C. with a heating mantle. The heat source was removed. The dropping funnel was charged with 57.28 g (0.294 moles, 1.00 equivalent) of the precursor, 2,2-dimethyl-3-trimethylsiloxy-1-propylchloride. The precursor was added dropwise, at an approximate feed rate of 0.6 ml/min. The reaction mixture was maintained at 65–68° C. with a dry ice/hexane bath. The total halide feed time was 105 minutes. The reaction was allowed to cool to and maintained at a temperature of 50° C. with a heating mantle. Then isoprene, 10.31 grams (0.151 moles, 0.51 equivalents), was added at an approximate feed rate of 0.5 ml/min. The temperature was maintained at 50° C. during the feed. The reaction mixture was allowed to stir for an additional 0.5 hours and maintained at a temperature of 50° C. with a heating mantle. The reaction mixture was then allowed to cool to room temperature. The reaction stirred for one hour before it was transferred to a medium porosity pressure filter. The lithium muds were washed with cyclohexane (1×14 ml). This afforded a clear, light yellow solution, 159.98 grams, approximately 200 ml.

Total base=33.0 wt. %.

Active base=32.0 wt. %.

Yield (based on active C-Li)=86.9%.

COMPARATIVE EXAMPLE

Preparation of 2,2-Dimethyl-3-trimethylsiloxy-1-propyllithium

No Chain Extension

A 500 ml. three-necked Morton flask was equipped with a mechanical stirrer, Claisen adapter fitted with a dry ice condenser and gas inlet, and a 125 ml. pressure-equalizing dropping funnel. This apparatus was dried in an oven overnight at 125° C., assembled hot, and allowed to cool to room temperature in a stream of argon. Lithium metal dispersion (lot #12393) was washed free of mineral oil with hexane (2×100 ml.) and pentane (1×100 ml.). The resultant lithium dispersion was dried in a stream of argon, weighed, 11.55 grams (1.66 moles, 2.80 equivalents) and transferred to the reaction flask with 140 ml. of cyclohexane. The mechanical stirrer was set at an agitation rate of 740 RPMs, and the reaction mixture was heated to 72° C. with a heating mantle. The heat source was removed. The dropping funnel was charged with 117.5 grams (0.594 moles, 1.00 equivalent) of the precursor (Lot 12422). The precursor was added dropwise, at an approximate feed rate of 1.29 ml/min. The reaction mixture was maintained at 68° C. with a dry ice/hexane bath. The total halide feed time was 100 minutes. The reaction was allowed to stir for an additional two hours with no additional heat. The solution was transferred to a medium porosity pressure filter. The lithium muds were washed with cyclohexane (2×25 ml). This afforded a light yellow solution, 130.2 grams. A larger amount of muds were present.

Total base=29.5 wt. %.

Active base=26.0 wt. %.

Chloride=110 ppm.

Yield (based on active C-Li)=34%.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A hydrocarbon composition comprising one or more protected functionalized chain extended anionic polymerization initiators of the formula

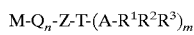

or of the formula

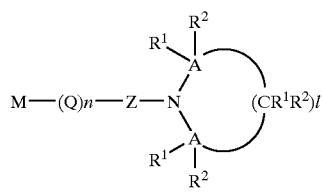

and at least one additional initiator comprises one or more non-chain extended compounds of the formula

or

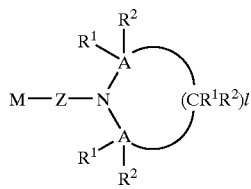

wherein:

M is lithium;

Q is a saturated or unsaturated hydrocarbyl group derived by incorporation of at least one conjugated diene hydrocarbons or mixtures thereof;

Z is a straight chain hydrocarbon connecting group which contains 3–25 carbon atoms;

T is oxygen;

A is carbon;

$(A-R^1R^2R^3)_m$ is a protecting group and $R^1$, $R^2$, and $R^3$ are alkyl;

n is >0 and <1; and m is 1.

2. The composition of claim 1, wherein said conjugated diene is selected from the group consisting of 1,3-butadiene, isoprene, 2,3-dimethyl-1,3-butadiene, 1,3-pentadiene (piperylene), myrcene, 2-methyl-3-ethyl-1,3-butadiene, 2-methyl-3-ethyl-1,3-pentadiene, 1,3-hexadiene, 2-methyl-1,3-hexadiene, 1,3-heptadiene, 3-methyl-1,3-heptadiene, 1,3-octadiene, 3-butyl-1,3-octadiene, 3,4-dimethyl-1,3-hexadiene, 3-n-propyl-1,3-pentadiene, 4,5-diethyl-1,3-octadiene, 2,4-diethyl-1,3-butadiene, 2,3-di-n-propyl-1,3-butadiene, 2-methyl-3-isopropyl-1,3-butadiene, and mixtures thereof.

3. The composition of claim 2, wherein Q comprises isoprene.

4. The composition of claim 1, comprising a protected functionalized chain extended anionic polymerization initiator of the formula

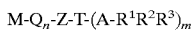

wherein:

M is lithium;

Q is derived by incorporation of isoprene;

Z is —(CH$_2$)$_3$—;

T is oxygen;

A is carbon;

$(A-R^1R^2R^3)_m$ is a protecting group; and each $R^1$, $R^2$, and $R^3$ is —CH$_3$; and m is 1.

* * * * *

UNITED STATES PATENT AND TRADEMARK OFFICE
CERTIFICATE OF CORRECTION

PATENT NO. : 6,770,587 B1
DATED : August 3, 2004
INVENTOR(S) : Schwindeman et al.

It is certified that error appears in the above-identified patent and that said Letters Patent is hereby corrected as shown below:

Title page,
Item [56], References Cited, U.S. PATENT DOCUMENTS, should include the following references:
-- 5,523,364   6/1996    Engel et al.
   5,527,753   6/1996    Engel et al.
   5,550,203   8/1996    Engel et al.
   5,565,526   10/1996   Schwindeman et al.
   5,605,872   2/1997    Engel et al.
   5,708,092   1/1998    Schwindeman et al.
   5,821,307   10/1998   Schwindeman et al.
   5,919,870   7/1999    Letchford et al. --

Column 14,
Line 35, should read -- $R^1,R^2,R^3,P,Q,Z,A,x,l,m$, and n have the meanings --

Column 26,
Line 4, should read -- $M\text{-}Z\text{-}T\text{-}(A\text{-}R^1R^2R^3)_m$ --

Signed and Sealed this

First Day of February, 2005

JON W. DUDAS
*Director of the United States Patent and Trademark Office*